United States Patent [19]
Lambeth et al.

[11] Patent Number: 5,840,984
[45] Date of Patent: Nov. 24, 1998

[54] STABILIZATION OF (HYDROCARBYLTHIO) AROMATIC AMINES AGAINST ODOR FORMATION

[75] Inventors: Gregory H. Lambeth; Paul L. Wiggins; William R. Brown, all of Baton Rouge, La.

[73] Assignee: Albemarle Corporation, Richmond, Va.

[21] Appl. No.: 880,547

[22] Filed: Jun. 23, 1997

[51] Int. Cl.⁶ .................................................. C07C 373/36
[52] U.S. Cl. ........................ 564/440; 546/290; 548/317.1; 548/484; 548/541; 548/543; 564/5; 564/300; 564/301; 564/305; 564/307; 564/315; 564/335; 564/426; 564/427; 564/428; 564/430; 564/437
[58] Field of Search ............................................... 564/440

[56] References Cited

U.S. PATENT DOCUMENTS

| | | | |
|---|---|---|---|
| 4,386,224 | 5/1983 | Deetman | 568/703 |
| 4,594,453 | 6/1986 | Ranken et al. | 564/440 |
| 4,595,742 | 6/1986 | Nalepa et al. | 528/64 |
| 4,670,597 | 6/1987 | Ranken et al. | 564/440 |
| 4,760,188 | 7/1988 | Ranken et al. | 564/440 |
| 4,866,209 | 9/1989 | Ranken et al. | 564/440 |
| 4,889,955 | 12/1989 | Ranken | 564/440 |
| 4,982,002 | 1/1991 | McKinnie et al. | 564/440 |

FOREIGN PATENT DOCUMENTS 59-42346  3/1984  Japan .

*Primary Examiner*—Richard L. Raymond
*Attorney, Agent, or Firm*—E. E. Spielman, Jr.

[57] ABSTRACT

Odor formation during storage of (hydrocarbylthio)aromatic amines due to formation and release of odoriferous sulfur-containing species such as dihydrocarbyldisulfides, is suppressed. To accomplish this, a small amount of N,N-dihydrocarbylhydroxylamine odor-inhibitor (e.g., N,N-diethylhydroxylamine) is blended with the (hydrocarbylthio)aromatic amine. This enables products such as a mixture of 3,5-di(methylthio)-2,4-diaminotoluene and 3,5-di(methylthio)-2,6-diaminotoluene) to be stored for long periods of time with significantly reduced formation and release of odoriferous sulfur-containing species.

31 Claims, No Drawings

STABILIZATION OF (HYDROCARBYLTHIO) AROMATIC AMINES AGAINST ODOR FORMATION

TECHNICAL FIELD

This invention relates to the inhibition of odor formation in (hydrocarbylthio)aromatic amines, especially during storage under ordinary ambient storage temperatures which in some parts of the world can reach as high as about 55° C.

BACKGROUND (Hydrocarbylthio)aromatic amines are useful as chain extenders in the production of polyurethanes. See in this connection U.S. Pat. Nos. 4,594,453; 4,595,742; 4,670,597; 4,760,188; 4,866,209; 4,889,955; and 4,982,002. By virtue of their chemical structure, (hydrocarbylthio)aromatic amines under storage conditions, especially for long periods of time and under relatively high storage temperatures can develop unpleasant odors. This apparently results from undesired reactions leading to the generation of odoriferous sulphur-containing species, particularly hydrocarbyl disulfides.

Attempts have been made to overcome this problem by use of certain inhibitors such as 4-methyl-2,6-di-tert-butylphenol. While some beneficial effect has been achieved, a need exists for a still more effective way of inhibiting such odor formation.

This invention is deemed to have fulfilled this need in a highly efficacious manner.

THE INVENTION

In accordance with one embodiment of this invention there is provided a method of inhibiting a (hydrocarbylthio) aromatic amine against odor formation, which method comprises mixing with the aromatic amine a small, effective odor-inhibiting amount of at least one N,N-dihydrocarbylhydroxylamine. Another embodiment of this invention is a composition which comprises (i) at least one (hydrocarbylthio)aromatic amine with which has been blended (ii) at least one N,N-dihydrocarbylhydroxylamine in an amount effective to inhibit odor formation during storage at ambient storage temperature(s).

Other embodiments and features of this invention will become still further apparent from the ensuing description and the appended claims.

(Hydrocarbylthio)aromatic amines suitable for use in the practice in this invention and methods for their preparation are described, for example, in U.S. Pat. Nos. 4,594,453; 4,595,742; 4,670,597; 4,760,188; 4,866,209; 4,889,955; and 4,982,002. Such compounds thus include (hydrocarbylthio) aromatic monoamines and (hydrocarbylthio)aromatic diamines. Of these, di(hydrocarbylthio)aromatic diamines having two hydrocarbylthio groups and two amino groups directly bonded to a mononuclear aromatic ring are preferred compounds, especially where the mononuclear aromatic ring also has one alkyl group directly bonded thereto. While the hydrocarbyl portion of the hydrocarbylthio groups of the foregoing compounds can be alkyl, alkenyl, cycloalkyl, cycloalkenyl, aryl, aralkyl, and like hydrocarbyl groups, aromatic amines in which the ring is directly substituted by one or more alkylthio groups are particularly preferred. The most preferred (hydrocarbylthio)aromatic amines are 3,5-di(methylthio)-2,4-diaminotoluene, 3,5-di(methylthio)-2,6-diaminotoluene, and mixtures of these two compounds.

The N,N-dihydrocarbylhydroxylamine stabilizers utilized in the practice in this invention have the formula RRNOH where each R is, independently, a hydrocarbyl group such as an alkyl, alkenyl, cycloalkyl, cycloalkenyl, aryl, aralkyl, etc., which typically contains up to about 18 carbon atoms and preferably up to about 8 carbon atoms; or where the two R groups taken together constitute a single divalent hydrocarbyl group bonded to the nitrogen atom such that the nitrogen atom is part of a heterocyclic ring, which single divalent hydrocarbyl group typically contains up to about 20 carbon atoms and preferably up to about 10 carbon atoms including the carbon atoms of one or more hydrocarbyl substituents that may be, but need not be, present on the heterocyclic ring. Since the single divalent hydrocarbyl group has two different carbon atoms singly bonded to the nitrogen atom, such group is, in effect, two individual hydrocarbyl groups joined together to form a heterocyclic group containing the nitrogen atom as the hetero atom. Thus for the purposes of this disclosure and the appended claims the term "N,N-dihydrocarbylhydroxylamine" includes, is intended to include, and should be clearly understood to include, such single divalent hydrocarbyl groups. Particularly preferred stabilizers are the N,N-dialkylhydroxylamines in which each alkyl group, independently, contains in the range of 1 to about 6 carbon atoms, and N,N-diaralkyl-hydroxylamines in which each aralkyl group, independently, contains in the range of 7 to about 14 carbon atoms. A few illustrative examples of these particularly preferred stabilizers include N,N-dipropylhydroxylamine, N,N-diisopropylhydroxylamine, N,N-dibutylhydroxylamine, N,N-diisobutylhydroxylamine, N,N-dipentylhydroxylamine, N,N-dihexylhydroxylamine, N,N-di(4-methylpentyl) hydroxylamine, N,N-dibenzylhydroxylamine, N,N-di(4-methylbenzyl) hydroxylamine, and N,N-di(2-phenethyl)hydroxylamine. The most preferred stabilizer for use in the practice of this invention is N,N-diethylhydroxylamine.

Methods for the preparation of N,N-dihydrocarbylhydroxylamines are known and reported in the literature. For example, N,N-diethylhydroxylamine can be produced by oxidation of triethylamine with hydrogen peroxide or a percarboxylic acid to form triethylamine oxide, which decomposes upon strong heating to form N,N-diethylhydroxylamine and ethylene, or by oxidation of diethyl amine with hydrogen peroxide or a percarboxylic acid, to form N,N-diethylhydroxylamine. N,N-diethylhydroxylamine is used in photographic developers, as an oxygen scavenger in high pressure boiler water systems, and as a radical chain stopping reactant in polymerization reactions. It has also been described as an inhibitor of discoloration in monoalkylphenols and in aromatic amines. N,N-diethylhydroxylamine and N,N-dibenzylhydroxylamine are listed in the *Aldrich Catalog Handbook of Fine Chemicals*, 1996–1997, at pages 517 and 460, respectively, and thus are presently available from at least one commercial source.

The compositions of this invention are readily formed by blending together the (hydrocarbylthio) aromatic amine and the N,N-dihydrocarbylhydroxylamine stabilizer in suitable proportions. Typically, odor-inhibiting amounts of the N,N-dihydrocarbylhydroxylamine odor stabilizer fall in the range of about 100 to about 10,000 parts per million parts (wt/wt) of the (hydrocarbylthio) aromatic amine. Preferred odor-inhibiting amounts fall in the range of about 1000 to about 5000 parts of odor stabilizer per million parts (wt/wt) of the (hydrocarbylthio)aromatic amine. It will be understood and appreciated from this disclosure that in any given situation where a departure from the foregoing numerical ranges is deemed necessary or desirable, such departure can be undertaken, and is entirely within the purview and scope of this invention.

While not required, the compositions of this invention can include one or more other components such as (i) one or more inert liquid solvents or diluents, (ii) one or more isocyanate prepolymers, (iii) one or more polyether polyols, (iv) one or more polyester polyols, (v) one or more plasticizers, (vi) one or more pigments, or the like. Suitable combinations of two or more of (i) through (vi) can be included in the compositions, if desired.

The following Examples illustrate the advantages achievable from the practice of this invention. These Examples are not intended to constitute limitations on the invention.

EXAMPLE 1

In order to determine the extent to which sulfur-containing odor forming bodies are produced during storage of a (hydrocarbylthio)aromatic amine, accelerated storage tests were conducted. In these tests the (hydrocarbylthio) aromatic amine used was a mixture of 3,5-di(methylthio)-2,4-diaminotoluene and 3,5-di(methylthio)-2,6-diaminotoluene. For these tests, this mixture was produced by distilling a product available commercially from Albemarle Corporation as ETHACURE® 300 curative. The N,N-dihydrocarbylhydroxylamine odor stabilizer used in these tests was N,N-diethylhydroxylamine. A blend was formed using proportions of 1000 ppm (wt/wt) of the stabilizer per million parts of the (hydrocarbylthio)aromatic amine and the blend was placed in a sealed test tube containing equal volumes of the liquid blend and air. A control sample of the uninhibited mixture of 3,5-di (methylthio)-2,4-diaminotoluene and 3,5-di(methylthio)-2, 6-diaminotoluene was also sealed in a test tube containing 50 volume percent of liquid and 50 volume percent of air. These samples were then stored for a period of 41 days at a constant temperature of 54° C. Upon completion of these tests the amount of dimethyldisulfide in the liquid phase of each sample was determined by gas chromatography. It was found that the uninhibited sample contained 20 ppm of dimethyldisulfide whereas the odor-inhibited sample of this invention contained only 3 ppm of dimethyldisulfide. Under these same test conditions it was found that 100 ppm of the odor stabilizer was insufficient to effectively stabilize this particular (hydrocarbylthio)aromatic amine mixture.

EXAMPLE 2

The procedure of Example 1 was repeated with the exception that the samples were stored in sealed test tubes containing 3 volumes of air per volume of liquid. In this case it was found that on completion of the test, the uninhibited (hydrocarbylthio)aromatic amine mixture contained 42 ppm of dimethyldisulfide. In contrast, the inhibited sample of this invention formed using 100 ppm of the odor stabilizer contained 34 ppm of dimethyldisulfide. The sample of this invention formed from 1000 ppm of the odor inhibitor was found to contain 13 ppm of dimethyldisulfide.

A further advantage of the practice of this invention is that in addition to achieving substantial reductions in odor-forming bodies during storage, the (hydrocarbylthio) aromatic amines undergo less color formation.

It is to be understood that the components referred to by chemical name or formula anywhere in the specification or claims hereof, whether referred to in the singular or plural, are identified as they exist prior to coming into contact with another substance referred to by chemical name or chemical type (e.g., another component, a solvent, or etc.). It matters not what preliminary chemical changes, transformations and/or reactions, if any, take place in the resulting mixture or solution as such changes, transformations, and/or reactions are the natural result of bringing the specified components together under the conditions called for pursuant to this disclosure. Thus the components are identified as ingredients to be brought together in connection with performing a desired operation or in forming a desired composition. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. Thus the fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

Each and every patent or publication referred to in any portion of this specification is incorporated in toto into this disclosure by reference, as if fully set forth herein.

This invention is susceptible to considerable variation in its practice. Therefore, the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

We claim:

1. A method of inhibiting a (hydrocarbylthio)aromatic amine against odor formation, which method comprises mixing with said amine a small, effective odor-inhibiting amount of at least one N,N-dihydrocarbylhydroxylamine.

2. A method according to claim 1 wherein said (hydrocarbylthio)aromatic amine is a (hydrocarbylthio) aromatic diamine.

3. A method according to claim 1 wherein said (hydrocarbylthio)aromatic amine is a di(hydrocarbylthio) aromatic diamine.

4. A method according to claim 3 wherein said di(hydrocarbylthio)aromatic diamine has two hydrocarbylthio groups and two amino groups directly bonded to a mononuclear aromatic ring.

5. A method according to claim 4 wherein said mononuclear aromatic ring also has one alkyl group directly bonded thereto.

6. A method according to claim 1 wherein said (hydrocarbylthio)aromatic amine is an (alkylthio)aromatic diamine.

7. A method according to claim 1 wherein said (hydrocarbylthio)aromatic amine is a di(alkylthio)aromatic diamine.

8. A method according to claim 7 wherein said di(alkylthio)aromatic diamine has two alkylthio groups and two amino groups directly bonded to a mononuclear aromatic ring.

9. A method according to claim 8 wherein said mononuclear aromatic ring also has one alkyl group directly bonded thereto.

10. A method according to claim 9 wherein said two alkylthio groups are methylthio groups and said alkyl group is a methyl group.

11. A method of inhibiting aromatic amine selected from (i) 3,5-di(methylthio)-2,4-diaminotoluene, (ii) 3,5-di (methylthio)-2,6-diaminotoluene, and (iii) a mixture of (i) and (ii) against odor formation, which method comprises mixing with said aromatic amine a small, effective odor-inhibiting amount of at least one N,N-dihydrocarbylhydroxylamine.

12. A method according to claim 11 wherein said aromatic amine is a mixture of 3,5-di(methylthio)-2,4-diaminotoluene and 3,5-di(methylthio)-2,6-diaminotoluene.

13. A method according to any of claims 1 through 12 taken individually wherein said N,N-dihydrocarbylhydroxylamine is N,N-diethylhydroxylamine or N,N-dibenzylhydroxylamine, or both of them.

14. A method according to any of claims 1, 6, 8, 11, and 12 taken individually wherein said amount is in the range of about 100 to about 10,000 parts of the N,N-dihydrocarbylhydroxylamine per million parts (wt/wt) of the (hydrocarbylthio)aromatic amine.

15. A method according to claim 11 wherein said aromatic amine is a mixture of 3,5-di(methylthio)-2,4-diaminotoluene and 3,5-di(methylthio)-2,6-diaminotoluene; wherein said N,N-dihydrocarbylhydroxylamine is N,N-diethylhydroxylamine; and wherein said amount is in the range of about 1000 to about 5000 parts of the N,N-dihydrocarbylhydroxylamine per million parts (wt/wt) of said mixture of 3,5-di(methylthio)-2,4-diaminotoluene and 3,5-di(methylthio)-2,6-diaminotoluene.

16. A composition which comprises (i) at least one (hydrocarbylthio)aromatic amine with which has been blended (ii) at least one N,N-dihydrocarbylhydroxylamine in an amount effective to inhibit odor formation during storage in the presence of air at ambient storage temperature (s).

17. A composition of claim 16 wherein said (hydrocarbylthio)aromatic amine is a (hydrocarbylthio) aromatic diamine.

18. A composition of claim 16 wherein said (hydrocarbylthio)aromatic amine is a di(hydrocarbylthio) aromatic diamine.

19. A composition of claim 18 wherein said di(hydrocarbylthio)aromatic diamine has two hydrocarbylthio groups and two amino groups directly bonded to a mononuclear aromatic ring.

20. A composition of claim 19 wherein said mononuclear aromatic ring also has one alkyl group directly bonded thereto.

21. A composition of claim 16 wherein said (hydrocarbylthio)aromatic amine is an (alkylthio)aromatic diamine.

22. A composition of claim 16 wherein said (hydrocarbylthio)aromatic amine is a di(alkylthio)aromatic diamine.

23. A composition of claim 22 wherein said di(alkylthio) aromatic diamine has two alkylthio groups and two amino groups directly bonded to a mononuclear aromatic ring.

24. A composition of claim 23 wherein said mononuclear aromatic ring also has one alkyl group directly bonded thereto.

25. A composition of claim 24 wherein said two alkylthio groups are methylthio groups and said alkyl group is a methyl group.

26. A composition of claim 16 wherein said amount is in the range of about 100 to about 10,000 parts of the N,N-dihydrocarbylhydroxylamine per million parts (wt/wt) of the (hydrocarbylthio)aromatic amine.

27. A composition consisting essentially of (A) aromatic amine selected from (i) 3,5-di(methylthio)-2,4-diaminotoluene, (ii) 3,5-di(methylthio)-2,6-diaminotoluene, and (iii) a mixture of (i) and (ii), with which has been blended (B) at least one N,N-dihydrocarbylhydroxylamine in an amount effective to inhibit odor formation during storage in the presence of air at ambient storage temperature (s).

28. A composition of claim 26 wherein said aromatic amine is a mixture of 3,5-di(methylthio)-2,4-diaminotoluene and 3,5-di(methylthio)-2,6-diaminotoluene and wherein said N,N-dihydrocarbylhydroxylamine is at least one N,N-dialkylhydroxylamine.

29. A composition of claim 27 wherein said amount is in the range of about 1000 to about 5000 parts of the N,N-dialkylhydroxylamine per million parts (wt/wt) of said mixture of 3,5-di(methylthio)-2,4-diaminotoluene and 3,5-di (methylthio)-2,6-diaminotoluene.

30. A composition of claim 26 wherein said aromatic amine is a mixture of 3,5-di(methylthio)-2,4-diaminotoluene and 3,5-di(methylthio)-2,6-diaminotoluene and wherein said N,N-dihydrocarbylhydroxylamine is N,N-diethylhydroxylamine or N,N-dibenzylhydroxylamine, or both of them.

31. A composition of claim 29 wherein said amount is in the range of about 1000 to about 5000 parts of the N,N-dialkylhydroxylamine per million parts (wt/wt) of said mixture of 3,5-di(methylthio)-2,4-diaminotoluene and 3,5-di (methylthio)-2,6-diaminotoluene.

* * * * *